United States Patent
Liu (12) United States Patent    (10) Patent No.: US 6,829,044 B2
Liu    (45) Date of Patent: Dec. 7, 2004

(54) COMPACT, HIGH-EFFICIENCY CONDENSATION NUCLEUS COUNTER

(75) Inventor: Benjamin Y. H. Liu, North Oaks, MN (US)

(73) Assignee: MSP Corporation, Shoreview, MN (US)

( * ) Notice: Subject to any disclaimer, the term of this patent is extended or adjusted under 35 U.S.C. 154(b) by 159 days.

(21) Appl. No.: 10/131,366

(22) Filed: Apr. 24, 2002

(65) Prior Publication Data

US 2003/0202169 A1 Oct. 30, 2003

(51) Int. Cl.[7] ............ G01N 1/00; G01N 37/00; H01J 40/14
(52) U.S. Cl. ............ 356/37; 73/28.01; 250/222.2
(58) Field of Search ............ 356/37, 337, 338; 73/28.01; 250/222.2

(56) References Cited

U.S. PATENT DOCUMENTS

| | | | |
|---|---|---|---|
| 3,592,546 A | 7/1971 | Gussman | 356/37 |
| 3,694,085 A | 9/1972 | Rich | 356/37 |
| 3,750,745 A * | 8/1973 | Moore, Jr. | 165/104.26 |
| 3,806,248 A | 4/1974 | Sinclair | 356/37 |
| 4,186,100 A | 1/1980 | Mott | 210/496 |
| 4,449,816 A | 5/1984 | Kohsaka et al. | 356/37 |
| 4,790,650 A * | 12/1988 | Keady | 356/37 |
| 4,950,073 A | 8/1990 | Sommer | 356/37 |
| 5,026,155 A | 6/1991 | Ockovic et al. | 356/37 |
| 5,118,959 A | 6/1992 | Caldow et al. | 250/573 |
| 5,239,356 A | 8/1993 | Hollander et al. | 356/37 |
| 5,519,490 A | 5/1996 | Nakata et al. | 356/338 |
| 5,675,405 A | 10/1997 | Schildmeyer et al. | 356/37 |
| 5,725,049 A | 3/1998 | Swanson et al. | 165/104.26 |
| 5,903,338 A * | 5/1999 | Mavliev et al. | 356/37 |
| 6,469,780 B1 * | 10/2002 | McDermott et al. | 356/37 |

* cited by examiner

*Primary Examiner*—Frank G. Font
*Assistant Examiner*—Roy M. Punnoose
(74) *Attorney, Agent, or Firm*—Westman, Champlin & Kelly, P.A.

(57) ABSTRACT

A condensation nucleus counter has a series of flow passageways forming a flow path, including a first passageway for carrying the gas stream having the particles to be detected which is preferably preheated A saturator is positioned to receive the flow of the gas stream and is made of a porous material of a controlled pore size having a portion immersed in a liquid working fluid. The liquid working fluid moves by capillary action along the length of the saturator. Vapor from the working liquid will be transferred to the gas stream as it moves through the saturator. The gas stream then passes to a condenser that reduces the temperature of the gas stream and causes the working fluid vapor to condense on the particles in the gas stream to form droplets that can be detected and counted.

22 Claims, 5 Drawing Sheets

COMPACT, HIGH-EFFICIENCY CONDENSATION NUCLEUS COUNTER

BACKGROUND OF THE INVENTION

This invention relates to a compact, high efficiency, and reliable condensation nucleus counter for counting aerosol particles and a method of using such counter. Specifically, the invention relates to the measurement of particles suspended in a gas, which is referred to as an aerosol. The most common gas is air, but other gases may also be the media for particle suspension. The particles can be solids, liquids, or a mixture of both. In all cases, a gas containing suspended particles is referred to as an aerosol, with no limitation being made as to the chemical nature of the particles and that of the gas, and their respective physical states.

Aerosols consisting of small particles suspended in air or other gases are widely encountered in nature and in the human environment. A widely used method for counting aerosol particles is the condensation nucleus counter (CNC), which is also referred to as a condensation particle counter. In a typical CNC, the aerosol first passes through a saturator to heat the gas and saturate the gas with the vapor of a working fluid. The gas is then cooled in a condenser to produce supersaturation. The supersaturated vapor then condenses on the particles to form droplets, which are counted by a light-scattering droplet counter.

Figure 1:
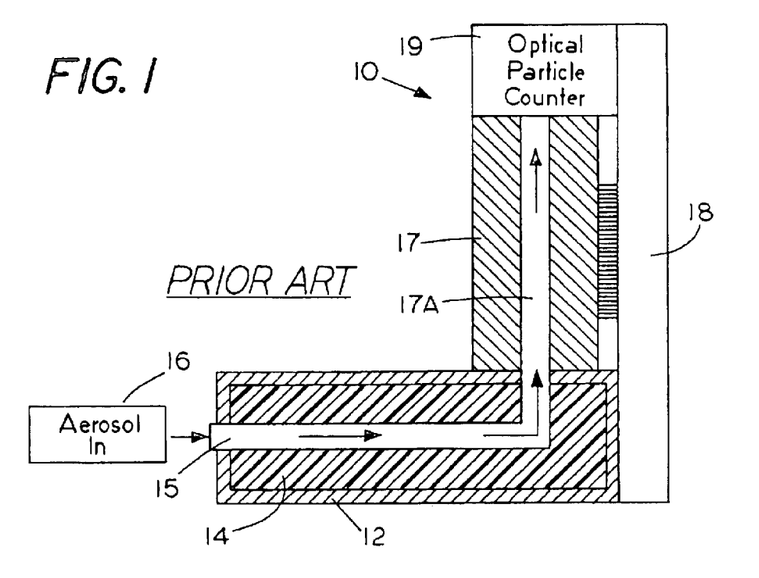
FIG. 1 is a schematic representation of a prior art condensation nucleus counter.
Figure 2:
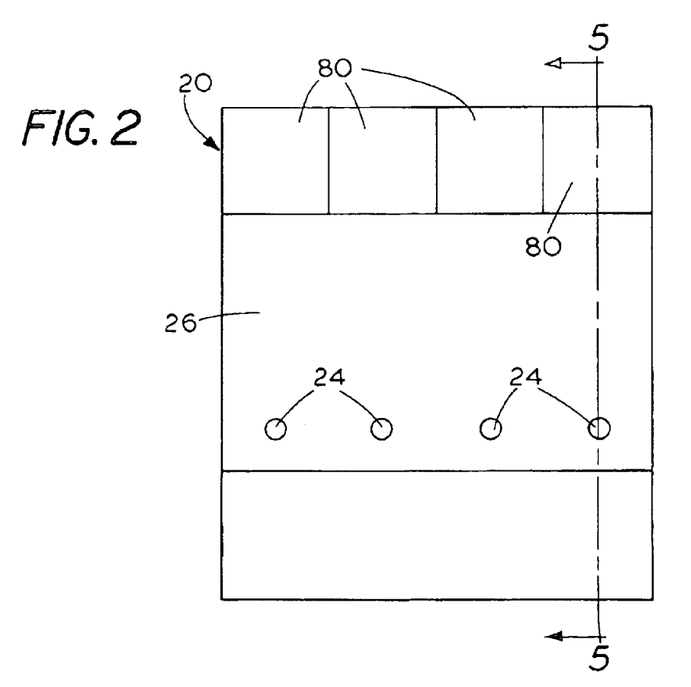
FIG. 2 is a front view of a multi-channel condensation nucleus counter (CNC) made according to the present invention.
Figure 3:
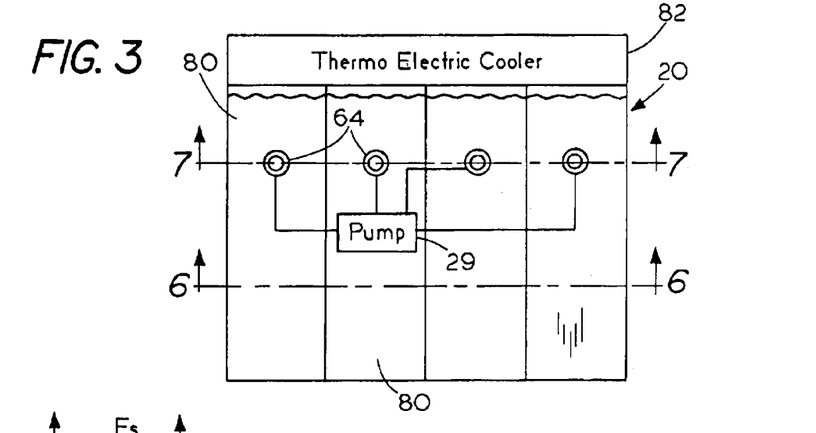
FIG. 3 is a top view of the CNC of FIG. 2.
Figure 4:
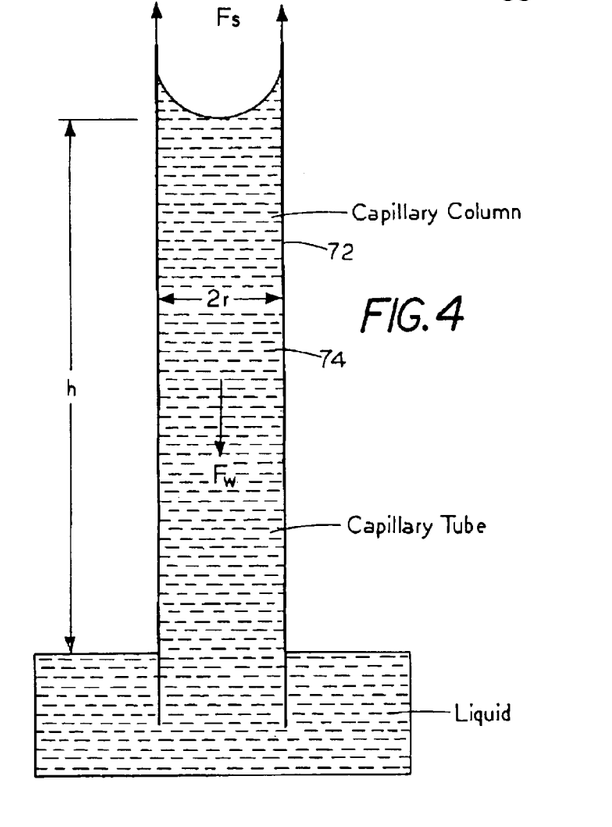
FIG. 4 is a schematic diagram showing the relationship between surface tension and liquid column rise.

A prior art CNC is schematically depicted in FIG. 1. The saturator comprises a porous plastic block placed in a heated liquid reservoir containing the working fluid in liquid form. A gas-flow passageway in the porous plastic allows the aerosol to flow through and be heated and saturated with the working fluid vapor. The condenser comprises a tubular passageway in a metal block kept at a low temperature. As the gas flows through the condenser passageway, it cools by transferring heat from the flowing gas stream into the cold passageway walls, thereby reducing the gas temperature and causing the gas to become supersaturated. The supersaturated vapor then condenses on the particles carried in the gas to form droplets. The aerosol flows into a conventional optical particle counter which then provides a droplet count, and hence indirectly the particle-count.

The condenser block is kept at a low temperature by a thermoelectric cooler. The heat rejected by the thermoelectric cooler is partly used to heat the liquid reservoir to the desired temperature and to heat the optics block of the optical particle counter to prevent vapor condensation therein, with the remaining heat being dissipated to the ambient air via a heat sink.

The most commonly used working fluid in a CNC is butyl alcohol. The saturator is usually heated to about 35° C., and the condenser is usually cooled to about 5° C. The prior art CNC of FIG. 1 is capable of detecting particles as small as 8 nanometers (nm) in diameter. With special designs, particles as small as 3 nm can be detected by the CNC.

In the prior art CNC depicted in FIG. 1, the heated aerosol flow passageway in the saturator block has a large rectangular cross-section to reduce the gas-flow velocity; thereby increasing the gas residence time for heating and saturating the gas with vapor. For the same reason, several tubular passageways are provided in the condenser block to reduce the gas flow velocity in each passageway and increase the residence time of the gas needed for cooling and vapor condensation on particles to form droplets. A CNC with these design features is described in U.S. Pat. No. 4,790,650.

The airflow velocity used in the prior art CNC is on the order of a few centimeters per second. The typical residence time is on the order of a second. The low airflow velocity causes the gas flow in the saturator and condenser passageways to be mostly laminar, or streamlined, in nature.

In laminar, or streamlined flow, gas passing through the condenser at different radial distances from the center of the passageway will move at different gas velocities. At the same time, heat and mass transfer by molecular diffusion across the gas flow will cause a temperature and vapor concentration gradient to develop, with the lowest gas temperature and vapor concentration being at the tube walls, and the highest, at the passageway centerline.

As particles at different radial distances flow through the condenser, the particles experience different temperature and vapor supersaturation conditions depending on the radial position of the particles. In general, particles passing near the center of the passageway would experience the highest supersaturation while particles passing through near the passageway walls would encounter lower supersaturation because of vapor depletion and direct vapor condensation on the cold passageway walls.

For this reason, to count very small particles, it is necessary to confine the gas flow containing particles to be detected to within a narrow region near the center of the tubular passageway. This is usually done by introducing the aerosol into the condenser passageway through a small hypodermic needle along the axis of the passageway. The commercially available ultrafine CNC for detecting particles down to 3 nm is based on this principle as described in "An Ultrafine Aerosol Condensation Nucleus Counter", M. B. Stolzenberg and P. H. McMurry, *Aerosol Science and Technology*, Vol. 14, pp. 48–65, 1991.

In the ultrafine CNC, the aerosol flow through the hypodermic needle is typically 10% of the total gas flow through the condenser. Therefore, the effective aerosol flow rate of the ultrafine CNC is reduced by a factor of 10 from that of a conventional CNC designed to detect larger particles. Because the ultrafine CNC needs two airflow streams in the condenser, the device is complicated.

Another issue related to the operation of a conventional CNC is that under high humidity conditions, gas flowing through the condenser may cool below the gas dew point to cause the moisture in the gas to condense. The condensed water then flows down the passageway walls to the porous saturator block, along with the condensed vapor of the working fluid.

When condensed water reaches the porous plastic in the saturator, it tends to accumulate in the saturator pores, thereby displacing the organic working fluid, from the porous material. Over time, sufficient water may accumulate in the porous material to cause the performance of the CNC to degrade, leading to improper functioning of the device, and giving rise to faulty and unreliable data. A method to separate the condensed water from the working fluid has been described in U.S. Pat. No. 5,118,959.

SUMMARY OF THE INVENTION

The present invention relates to improvements in handling an aerosol in a CNC to improve performances. The saturator has a porous metal insert forming the gas passageway with controlled pore size so that the saturator can be placed in any orientation, other than the traditional horizontal, or near horizontal position.

An appropriate pore size is selected so that a higher pressure difference can be sustained across the porous material without the liquid being blown out from the pores.

The flow passageways are designed to cause turbulent eddies to increase the rate of heat and vapor transfer in the saturator and condenser to make the device smaller, with improved overall performance.

The working fluid is kept in one reservoir, while the condensate (working fluid and water) is collected in a separate reservoir in order to eliminate problems associated with condensed water permeating through the porous material of the saturator.

Also, the present invention comprises a multi-channel CNC that would allow several sample streams to be counted simultaneously by the CNC.

DETAILED DESCRIPTION OF THE ILLUSTRATIVE EMBODIMENTS

In FIG. 1, as previously mentioned, a prior art condensation nucleus counter (CNC) is illustrated at 10, and includes a fluid reservoir 12 that is lined with a porous plastic material 14. Aerosol from a source 16 is introduced into a passageway 15 in the center of the porous plastic and the passageway makes a right angle bend and goes upwardly through a condenser block 17, through a condenser passageway 17A. The aerosol from the source contains water vapor as well. The block 17 is cooled with a thermoelectric module 19, placed between block 17 and a heat sink 18. The thermoelectric module 19 extracts heat from the condenser block 17 and provides for a reduction in temperature so that the aerosol passing through the passageway 17A becomes saturated with vapor from the working fluid in the fluid reservoir, and then the working fluid vapor is condensed as the aerosol passes through the passageway 17A. An optical particle counter 19 is used for counting the droplets that are formed on the particles after condensation.

In FIGS. 2–7 a condensation nucleus counter (CNC) made according to the present invention is illustrated at 20. The counter is a multiple channel CNC, with each channel identical to the channel shown in FIG. 5. Air, or some other gas, containing particles to be detected and some water vapor from an aerosol source 22, first flows in a path through a heated passageway 24 in a metal block 26 that is in close thermal contact with the saturator chamber 28. The aerosol flow is established by a pump or other flow generator 29 at an outlet of each CNC section. The saturator chamber 28 comprises a passageway in a saturator tube 30 made of porous metal. The aerosol, moving through the passageway 24 is thus preheated to nearly the same temperature as the saturator chamber 28 before it enters the chamber in the saturator tube 30. Preheating the gas sample before having it move through the chamber 28 reduces the need to heat the gas in the saturator, as is done in a conventional saturator shown in FIG. 1, and used with the prior art CNC. Preheating the aerosol reduces the size of the saturator section and improves the overall performance of the saturator.

In addition, when the gas sample flows through heated passageway 24, in which heat is transferred from the walls forming the passageway to the gas, the thermophoretic force acting on the particles greatly reduces or eliminates particle loss caused by diffusion to the walls of the passageway 24. Even very small particles with a high diffusion coefficient, such as those in the nanometer size range, would suffer little or no loss of particles during their passage through the pre-heating passageway 24.

The saturator tube 30 comprises a porous metal tube, preferably porous stainless steel, inserted into the metal block 26 in heat conducting relationship to the block. The metal block 26 is heated electrically with a small electric heater 34, or a thermoelectric heater, and kept at an elevated temperature. The porous metal saturator tube temperature is typically between 25 to 40° C., when butyl alcohol is used as the working fluid in the condensation nucleus counter.

The lower end of the porous metal saturator tube 30 is in contact with a working fluid in liquid form 36 in a working fluid reservoir 38. A solid plug 40 in the saturator tube 30 separates the lower part 30A of the porous metal tube from the upper part 30B The saturator pore size in porous metal saturator tube is selected so that the liquid will be drawn by capillary surface tension force to fill the interstitial pore spaces and saturate the porous metal saturator tube 30 thoroughly over its entire length.

The space above the solid plug 40 is surrounded by the porous metal tube and forms saturator chamber 28. As the gas flows into chamber 28 it encounters working fluid vapor being vaporized from the wet porous saturator tube walls.

At the entrance or inlet to the saturator tube 30 there is a small orifice 44 or multiple orifices as shown, through which aerosol flows. The small area of the orifice 44 causes the aerosol to form a high velocity gas jet as it flows through the orifice. The orifice size is selected so that the average jet velocity is typically 10 m/s (meters per second). This high velocity gas jet then impinges into the relatively stagnant gas in the heated saturator chamber 28. As the gas jet impinges into the chamber 28 it mixes with the heated and vapor-laden gas in the chamber by turbulent mixing. As a result, the gas itself quickly becomes saturated with the working fluid vapor.

The aerosol, now saturated with the vapor of the working fluid, then leaves the saturator tube through a heated passageway in tube 42 to a condenser 50. The aerosol flow into the passageway in condenser 50 is also through a small orifice 52, (which can be one or more openings as shown) in the side wall of tube 42. The end of tube 42 is blocked so the gas must exit through the orifice 52.

The gas exits the orifice at an average gas velocity that is typically 10 m/s. The small cylindrical chamber 54 of the condenser 50, or a chamber of some other geometrical cross section shape, is kept at a low temperature, typically 5° C. to 15° C., when butyl alcohol is used as the working fluid 36. As the aerosol mixes with cold air in the condenser chamber 54 by virtue of the turbulent mixing action created by the high-velocity aerosol jet, the aerosol quickly cools and becomes thermally equilibrated with the cold chamber gas to produce condition of supersaturation for vapor condensation and droplet growth. Water vapor and excess working fluid vapor condense out of the aerosol and will drain out a drain hole 51 into a condensate tank 53. Condensate 55 collects in the tank 53.

The grown droplets in the aerosol are then carried by the airflow through a tubular nozzle 56 into a droplet counter section 58 for detection by a light scattering droplet counter. The individual droplets can be counted with appropriate electronic circuitry. The light scattering droplet counter has a chamber 59, and includes a laser light source 60 that projects a laser beam through a condensing lens 62 that focuses the beam. The aerosol carrying the liquid droplets carried through the nozzle 56 crosses the focus region of the beam and exits chamber 59 through an outlet tube 64. Light scattered by the droplets is collected by a collector lens 66 and projected to a light sensitive photo-diode 68, which provides light signals to a pulse height analysis circuit 69 for counting. The lens 66 has a center beam stop 70, so only scattered light is collected and sensed by photo-diode 68 and circuit 69.

In the prior art CNC the porous material used as the saturator block in the liquid working fluid reservoir has unspecified physical characteristics, other than the fact that the material must be porous. To work efficiently as a saturator, the interstitial pore space must be fully saturated with liquid comprising the working fluid, so that the liquid may permeate throughout the porous material, especially to the surface of the aerosol passageway where vaporization takes place. In spite of the importance of having a fully saturated porous material for the working fluid, there has been no attention paid to the specific pore size that must be used to fully saturate the porous material with the working-fluid liquid. The physical basis for selecting the appropriate pore size for saturator design is described in this invention.

The porous metal that forms tube 30 of the saturator chamber 28 in the present invention is selected to have a preferred pore size so that liquid filling the pores may be lifted by capillary surface tension force to a desired height. In addition, when there is the need to sustain a certain minimum gas pressure difference across the liquid-saturated porous metal tube 30, the pore size can be selected by the method described herein so that the liquid filling the pores can sustain the gas pressure and not be blown out from the pores.

FIG. 4 shows a schematic diagram of a small capillary tube 72 of a radius, r, filled with a liquid that wets the surface of the walls of capillary tube 30. This capillary tube 72 represents an equivalent pore in the wall of saturator tube 30. Metals, such as stainless steel, are wettable by water, and are referred to as hydrophilic. Many organic liquids, such as butyl alcohol used as a working fluid in a CNC, would also wet the metal surface. For liquids that wet the surface of the capillary, the surface tension of the liquid would exert a lifting force, $F_s$, on the liquid column 74 according to the equation:

$$F_S = 2\pi r\sigma$$

thereby lifting the liquid column to a height, h, shown in FIG. 4, where is the surface tension of the liquid. The liquid column being lifted by surface tension has a weight $$F_W = \pi r^2 \rho g h$$

At equilibrium, the surface tension force, $F_s$, would be balanced by the liquid column weight, $F_w$, i.e.

$$F_S = F_W$$

Thus, the equilibrium capillary-column height is $$h = \frac{2\sigma}{r\rho g}$$

where ρ is the density of the liquid (working fluid) and g is the acceleration of gravity. The following table shows the relationship between the height, h, to which a liquid can be lifted by surface tension for various pore sizes. It is assumed that the liquid surface tension is 30 dyne/cm and the liquid density is 1 g/cc. These property values are close to those for the working fluid used in a typical CNC.

TABLE 1

| σ, dyne/cm | Pore Dia., μm | h, cm $H_2O$ |
|---|---|---|
| 30 | 1.0 | 1,223 |
| 30 | 2.0 | 612 |
| 30 | 5.0 | 245 |
| 30 | 10.0 | 122 |
| 30 | 20.0 | 61 |
| 30 | 50.0 | 24 |
| 30 | 100.0 | 12 |
| 30 | 200.0 | 6 |
| 30 | 500.0 | 2 |
| 30 | 1000.0 | 1 |

The result in the above table shows that for a pore diameter of, say, 10 μm, the capillary surface tension force is capable of lifting a liquid column to a height of 122 cm. A vertical porous metal tube such as saturator tube 30 will thus have its pores filled by the liquid up to that maximum height. This attainable height is much longer than what is needed for the saturator tubes in a CNC. A typical CNC may need an overall saturator length on the order of a few centimeters. An overall saturator tube length of 15 cm is likely to be more than adequate for most applications. Consequently, considerably larger pore diameters can be used.

If the capillary is connected to a source of gas on the top at a pressure, Δp, above the ambient, this gas pressure would exert a force on the capillary column below $$F_p = \pi r^2 \Delta p$$

When this force is equal to or larger than the surface tension force, $$F_S = 2\pi r\sigma$$

the capillary column would be blown out from the bottom which is assumed to be in liquid 36 in a liquid reservoir. The maximum gas pressure that can be applied to the capillary column is thus given by $$(\Delta p)_{max} = \frac{2\sigma}{r} = \rho g h$$

The capillary-column rise value shown in Table 1 above is directly related to the maximum gas pressure that can be impressed across the wall of the porous metal tube 30 without the liquid (working fluid) being forced out of the pores. As results show, a porous metal tube with 10 $\mu$m diameter pores and filled with an organic liquid with a capillary column rise of 122 cm would be capable of sustaining a maximum gas pressure difference of 122 cm water gage across the porous metal tube.

Since porous metals are generally wettable by most organic liquids useful as working fluid in a CNC, they can sustain considerable gas pressure difference before the liquid is blown out from the pores. In addition, porous metals can be manufactured with much smaller pore sizes than porous plastics and are more consistent in quality and have more uniform pore sizes than porous plastics. Using porous metal, especially porous stainless steel, would thus make it possible to design CNC saturators with very predictable capillary column rise values. The performance of saturators made from porous metals would thus be more consistent and more predictable.

In the present invention, gas carrying fine particles for detection (the aerosol) enters the saturator chamber 28 at a high velocity through a small orifice or orifice set 44. As the high-velocity gas jet impinges into the saturated and heated gas in the chamber 28, it breaks up into small turbulent eddies whose size is on the order of the opening size of the orifice 44. The small turbulent eddies quickly disperse into the heated and vapor-saturated gas in chamber 28. Through heat and vapor diffusion across the eddy boundaries the individual eddies become heated and saturated with the vapor. The time scale over which thermal and vapor diffusion takes place can be estimated from the Einstein's equation for heat and vapor transport by molecular diffusion. For thermal diffusion, the time scale is given by the equation $$x^2 = 2\alpha t_t$$

and for vapor diffusion it is $$x^2 = 2Dt_v$$

where x is the root-mean-square diffusion distance, $t_t$ and $t_v$ are the characteristic thermal and vapor diffusion times, $\alpha$ is the thermal diffusivity of the gas, and D is the diffusivity of the vapor.

The characteristic thermal and vapor diffusion times across the eddy boundaries thus vary as the square of the radius of the turbulent eddies. Since the radius of the turbulent eddies, x, is of the same order of magnitude as the orifice 44 radius, r, i.e., $$x \approx r$$

and since the average gas velocity through the orifice is $$V_g = \frac{Q}{\pi r^2}$$

the characteristic thermal and vapor diffusion times are $$t_t = \frac{Q}{2\pi\alpha V_g}$$

and $$t_v = \frac{Q}{2\pi D V_g}$$

where Q is the volumetric gas flow rate through the orifice. Both $t_t$ and $t_v$ are thus inversely proportional to the average gas velocity, $V_g$, through the orifice.

By way of an example, for a gas flow rate of 300 cc/min, an orifice 44 with a diameter of 0.75 mm, the average gas velocity through the orifice is 10 meters per second. The characteristic eddy size is 0.75 mm, and the characteristic diffusion times are on the order of 36 milliseconds. For comparison, the prior art laminar flow saturator used for vapor saturation generally involve gas residence time in the saturator that is on the order of one second in order for the gas to be heated and saturated by the vapor of the working fluid. Using the turbulent jet approach described herein the characteristic thermal and vapor diffusion times are reduced considerably, by a factor of approximately 30. By increasing the gas velocity to say, 20 m/s, the thermal and vapor diffusion times can be further decreased by a factor of two, to approximately 16 millisecond, or a factor 60 higher than the laminar flow saturator used in the prior art CNC shown in FIG. 1.

The process occurring in the turbulent-mixing condenser 50 is similar. As the heated and saturated gas carrying fine particles enters the condenser through a small orifice or orifice set 52, the gas is also broken up into small eddies. These small eddies, each containing heated and saturated vapor, are dispersed into the cold gas in the passageway or chamber 54 near the condenser temperature. The individual eddies are cooled by thermal diffusion through the eddy boundaries, creating conditions of supersaturation that gives rise to vapor condensation and droplet growth on the particles.

Since heat diffusion occurs more quickly than vapor diffusion for the organic working fluid vapor, the individual eddies would be cooled to a near uniform temperature before much vapor is lost by diffusion across the eddy boundary to the surrounding cold gas. This insures that the conditions of supersaturation created within each eddy for vapor condensation and droplet growth are nearly uniform and that all particles of the same size are activated. This would lead to improved performance of the CNC. In addition, the loss of working fluid by vapor condensation on the cold condenser tube walls forming chamber 54 is minimized. The resulting working fluid consumption by the CNC is also less. The size of the working fluid reservoir 38 can thus be reduced, leading to an overall reduction in the size of the CNC.

The gas velocity entering the saturator and condenser chambers needed to create efficient turbulent mixing depend on how quickly the mixing needs to take place. For CNC applications, it has been found that a gas jet velocity of 10 m/s, and even gas velocities as low as 50 cm/s, can be used to improve the performance of the CNC.

Although only one orifice 44 or 52 may be used for turbulent gas mixing in the saturator or the condenser, more than one orifice may be used. For instance, if four orifices of the same diameter are used instead of one single orifice while the volumetric rate of gas flow into the condenser, or the saturator, and the average gas velocity through each orifice remain unchanged, the area of each orifice must be reduced by a factor of four, and the orifice diameter by a factor of two. The orifice diameter can thus be reduced from 0.75 mm to 0.375 mm, thus reducing the characteristic thermal diffusion time from 36 milliseconds to 18 milliseconds. Increasing the number of orifices, say, from one to sixteen, would further reduce the orifice size from 0.75 mm to 0.19 mm and the characteristic thermal diffusion time from 36 milliseconds to 9 milliseconds. By increasing the number of orifices used at the saturator or the condenser inlet, the number of turbulent eddies is greatly increased. At the same time, the eddy size becomes smaller thereby reducing the time needed for thermal and vapor equilibration.

To count the droplets formed by condensation, the optical particle counter can be used. In the preferred embodiment shown in FIG. 6, a light-scattering droplet counter 58 (LDC) is used as described. In the LDC, the condensing lens 62 is a cylindrical lens that brings the laser beam to focus in a region 61 at the axis of the inlet nozzle 56 and the outlet tube 64. As the beam reaches the collecting lens 66 the beam stop 70, which is an opaque, light-absorbing surface, the laser light is absorbed.

Figure 6:
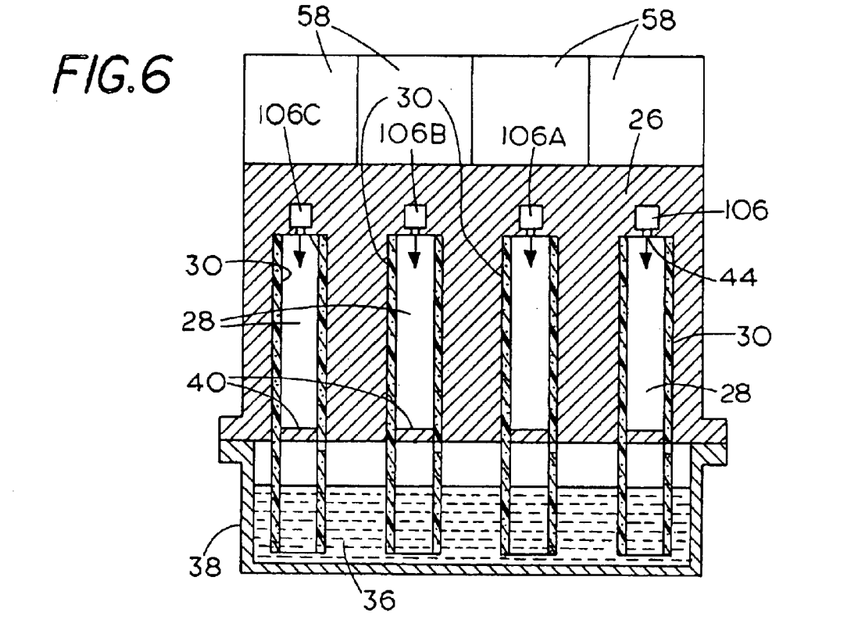
FIG. 6 is a sectional view taken on line 6—6 in FIG. 3.

The droplet aerosol passes into the LDC through the inlet nozzle 56. When the droplets reaches the nozzle tip, the cross-sectional flow area is greatly reduced, and the aerosol is accelerated to a high velocity. This high velocity gas, containing droplets to be detected, then passes through the focused laser beam and flows out of the light-scattering particle counter through the outlet tube 64. As each droplet passes through the focus region 61 of the laser beam, it scatters light in all directions. The collecting lens 66 then collects the scattered light in the forward direction of the laser beam and within the angular range subtended by the lens 66 onto the solid-state photo-diode detector 68. The signal from the photo-diode 68 is then processed electronically by a suitable pulse height analysis circuitry 69. Although a single lens is shown as the collecting lens 66 for scattered-light, it is understood that more than one lens, or a multi-element lens, can be used as the collector to improve the performance.

Both the condensing and collecting lenses shown are shown as single lenses for simplicity, it is understood that more than one lens may be used to improve the optical performance of the LDC 58. Such improvements are easily understood by those skilled in the art of the optical design of light-scattering particle counters.

To prevent working fluid vapor condensing on the LDC optics, the LDC housing 80 is made of a heat conductive material, such as aluminum, and placed in close thermal contact with the saturator block 26 and heated to substantially the same temperature as the saturator block 26. The need to prevent vapor condensation on the optics of the droplet detector is understood by those skilled in the art of designing CNCs as shown by the apparatus drawing in U.S. Pat. No. 4,790,650 (Keady).

Figure 5:
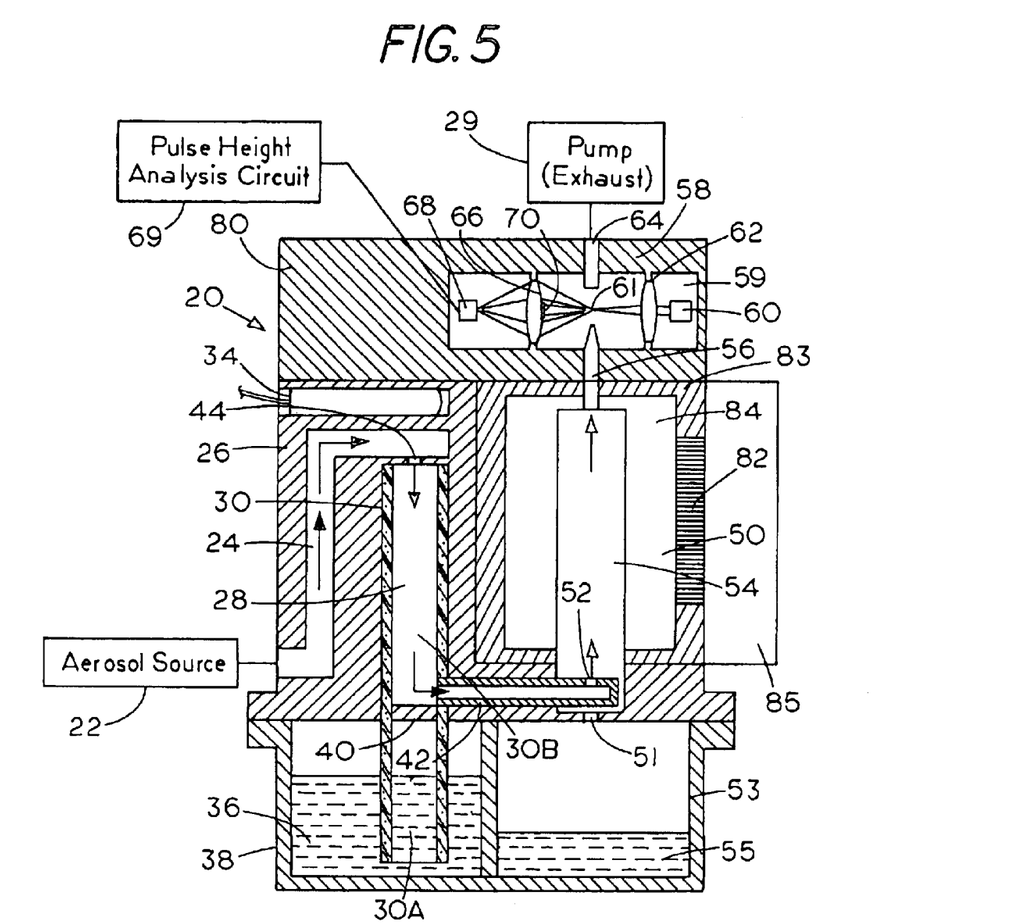
FIG. 5 is a sectional view taken on line 5—5 in FIG. 2.

In the preferred embodiment of the CNC shown in FIG. 5, an electric heater 34 is used to heat the saturator block to the desired temperature, typically 35° C., and a thermoelectric cooler 82 is used to cool the condenser block 84 forming part of condenser 50 to the desired temperature, typically 5° C.

FIG. 5 shows a single channel from a multi-channel CNC shown in FIGS. 2, 3, 6 and 7 that would be suitable for such purposes.

Four measuring channels are shown in FIGS. 2, 3, 6 and 7, each of which is numbered identically to FIG. 6, a single channel, except the flow passageways are numbered 106, 106A, 106B and 106C. In general, a multi-channel CNC may have as few as two measuring channels. There is no specific upper limit as to the maximum number of channels a multi-channel CNC may have. The upper limit is generally determined by space and cost considerations.

FIG. 6 shows a section through the saturator metal block 26 containing the porous metal saturator tubes 30. The porous metal saturator tubes 30 are all in close thermal contact with the saturator block 26, which is made of a metal of high thermal conductivity, typically aluminum. The block 26 is heated with electric heaters 34 to a suitably high temperature, typically from 25° C. to 40° C. Since the saturator metal block 26 is at a substantially uniform temperature, all of the saturator tubes 30 are also at a temperature that is substantially the same.

The lower ends of the saturator tubes 30 are in fluid communication with the working fluid 36 in the working fluid reservoir 38. The same reservoir 38 is used to supply the working fluid to all the saturator tubes. By capillary surface tension, the porous metal saturator tubes 30 thus become saturated with the working fluid in their interstitial pore spaces, thus allowing the working fluid to vaporize into the saturator chambers 28 from the porous metal walls. Each porous metal saturator tube 30 has a solid plug separator forming the base of the saturator chamber 28, while the lower end of the saturator tube 30 dips into the working fluid 36 in the reservoir 38. Again, a small orifice 44 is used at the gas inlet to the saturator chambers 28, to enable the gas containing particles to be detected to form a high gas velocity jet for turbulent gas mixing and vapor saturation in the saturator chamber 28.

Figure 7:
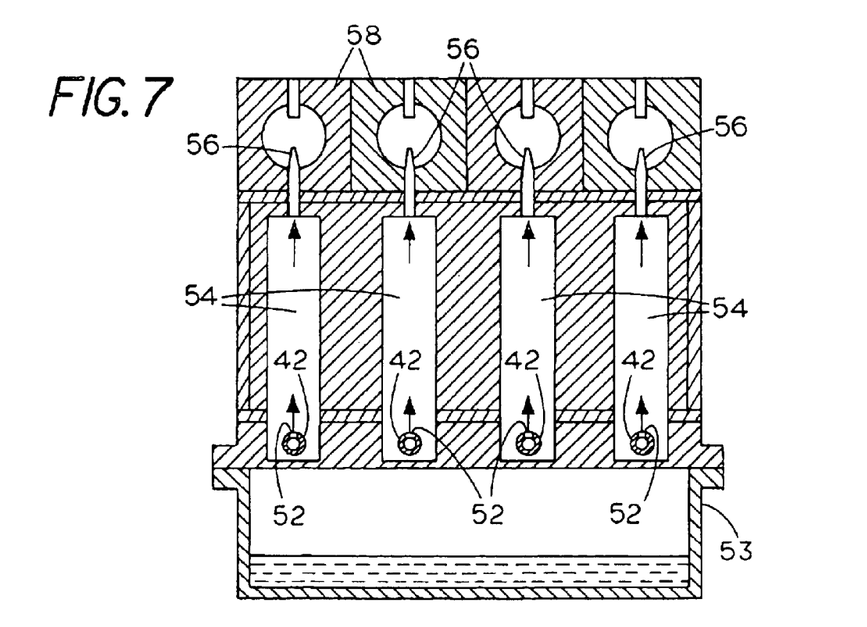
FIG. 7 is a sectional view taken on line 7—7 in FIG. 3.

FIG. 7 shows a section through the condenser block 84, which is also made of a material of high thermal conductivity, typically aluminum. The block 84 is cooled with a thermoelectric cooler 82, which is shown in FIG. 5, to a temperature that is typically 5° C. The condenser block 84 is surrounded by thermal insulation 83 to minimize the heat-load on the thermo-electric cooler 82 to minimize the electrical power required to operate the thermo-electric cooler 82. A heat sink 85 is also provided.

There are a multitude of condenser cavities or chambers 54 in the condenser block. Each chamber 54 is typically of a generally cylindrical shape. At the base of each chamber, there is a heated gas passageway in tubes 42 carrying the heated and vapor-laden gas containing particles to be detected from the saturator 28. This gas flows through the small inlet orifice 52 to form a high velocity gas jet that impinges into the condenser chambers 54 to cause turbulent mixing and vapor condensation on the particles to form droplets. Some water and working liquid also condenses and drains through openings 51 into the drain chamber 53. The droplets are then carried by the gas through the chamber outlet and into the inlet nozzle 56 in the droplet counters 58 on the top of the CNC. There is one droplet counter for each CNC channel. For the four-channel CNC shown, there are thus four separate droplet counters 58.

Figure 8:
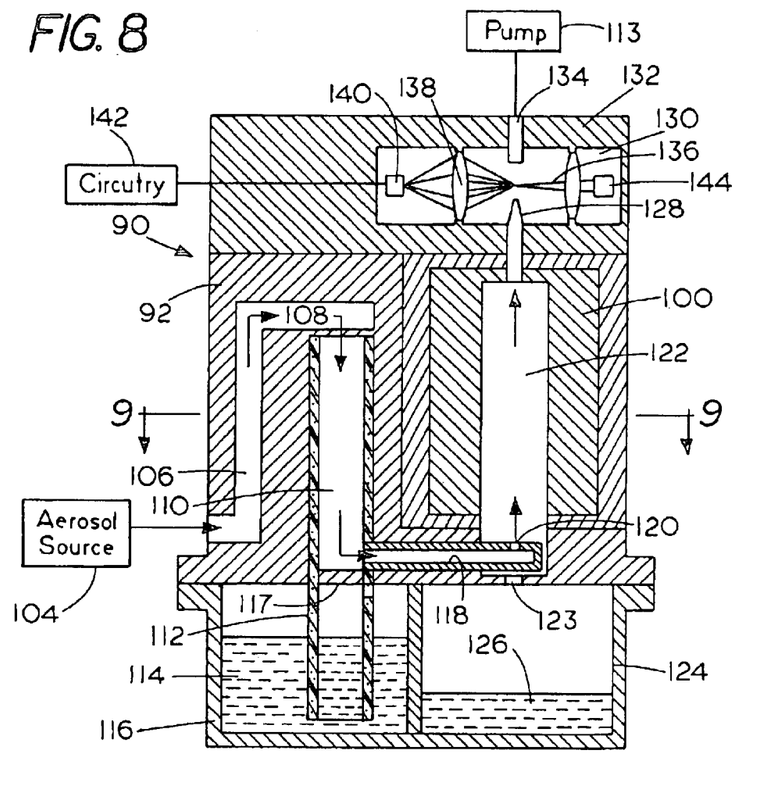
FIG. 8 is a vertical sectional view of a modified CNC of the present invention.
Figure 9:
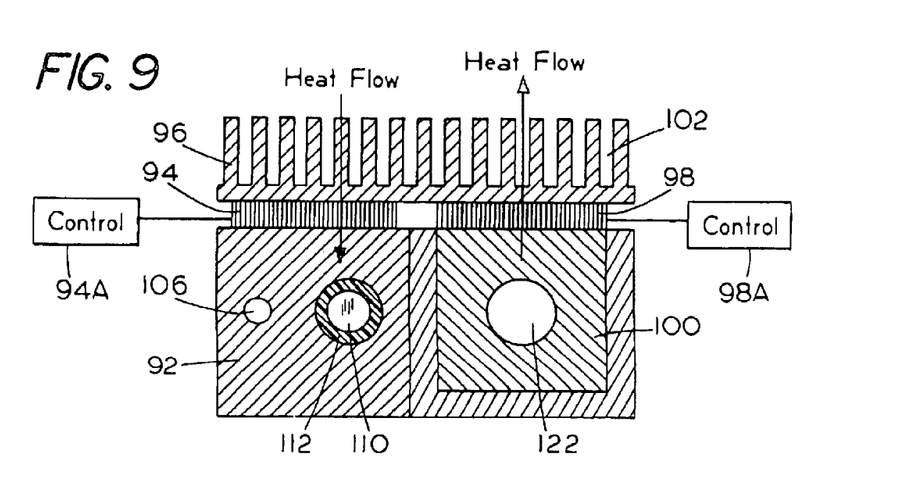
FIG. 9 is a sectional view taken on line 9—9 in FIG. 8.

Another embodiment of the CNC of the present invention is shown in FIGS. 8 and 9 at 90. The operation and construction is substantially the same as in FIG. 5, except the electric heater has been eliminated and replaced with a thermoelectric heater and the thermoelectric cooler and the heat sink have been moved to a new location.

In FIGS. 8 and 9, the CNC 90 has a saturator block 92 that is heated by a thermoelectric heater 94 that draws heat from the ambient air through a heat sink 96 and rejects heat (or adds heat) to the saturator block 92. A thermoelectric cooler 98 is used to draw heat from a condenser block 100 while rejecting heat to the ambient air through a heat sink 102. The condenser block 100 is provided with insulator layers on the sides other than the surface in contact with thermoelectric cooler 98. The two heat sinks 96 and 102, one for the thermoelectric heater 94 and the other for the thermoelectric cooler 98, are coupled thermally and form a single unit, so that the heat rejected by one is used to supply the heat drawn by the other. In this way, the electrical energy needed to heat the saturator block 92 is reduced, since part of the heat for heating the saturator comes from the heat rejected by the thermoelectric cooler for the condenser, the balance being supplied by the electrical power input to the thermoelectric heater.

In the embodiment of FIGS. 8 and 9, the aerosol source 104 provides the aerosol to a condenser passageway 106 in the condenser block 92, and then the aerosol passes through an orifice 108, into a saturator chamber 110 formed in a porous metal saturator tube 112 constructed as previously explained of a porous metal. The aerosol flow is established by a pump or other differential pressure causing flow generator 113 at an outlet of the CNC 90. The porous metal saturator tube has an end that is in a working fluid in liquid form 114, held in a reservoir 116 and is blocked with a wall 117. The aerosol, after saturation by the vapor of the working fluid, flows in a path, into a tube 118, and through an orifice or orifice set 120 into a condenser chamber 122 of the condenser block 100.

It should also be noted that there is a drain opening 123 leading to a condensate chamber 124 for collecting condensation 126.

The aerosol carrying the droplets with condensation formed around the particles passes through an outlet nozzle tube 128 into a light scattering droplet counter chamber 130 of a light scattering droplet counter 132. An outlet tube 134 connected to pump 113 permits the aerosol to exit the chamber 130, after it has passed through a laser beam 136. Light scattered by the droplets is collected by a lens 138 that provides light signals to a photo-diode 140, as previously explained. The photo-diode 140 is also connected to suitable circuitry 142 also as previously explained for providing a droplet (particle) count. The laser light beam 136 comes from a laser source 144.

One advantage of using a thermoelectric heater 94 for heating the saturator block 92 as opposed to a simple electric heater is that when a CNC is used in a severe temperature environment, when the ambient temperature is higher than the desired operating temperature of the saturator, the thermoelectric heater can be used as a cooler by simply reversing the direction of the DC current flow to the heater. For instance, if the ambient temperature is 35° C., while the desired operating temperature of the saturator is 30° C., a simple electric heater would be unable to keep the saturator at the desired 30° C. level, while a thermoelectric heater can be used in the cooling mode by simply reversing the direction of the DC current flow. By this means, the operating temperature range of the CNC can be extended to accommodate the more severe temperature environment that may sometimes occur.

Another advantage of using two thermoelectric modules, one used primarily as a heater and the other as a cooler, in a "push-pull" mode is that the two separate thermoelectric modules can be controlled independently in order to control the temperature of the saturator and the condenser at their respective set-point levels, say 35° C. and 5° C. In the conventional approach, where a single thermoelectric module is used between the condenser and the saturator, only the temperature difference between saturator and the condenser can be controlled. As the ambient temperature varies, the actual temperature of the condenser block 100 and that of the saturator block 92 would also vary, leading to performance variation of the CNC. This variation can be eliminated by using separate independent controls 94A and 98A for the two separate thermoelectric modules 94 and 98. Control 94A is used to control module 94 and control 98A is used to control module 98.

As to the specific means for controlling the temperature of the saturator block 92 or the condenser block 100 through a thermoelectric module, the usual practice is to measure the difference in the actual temperature and the desired set-point, and, through a PID (proportional-integral-differential) controller, vary the applied voltage to vary the current flow through the thermoelectric module until the temperature difference is reduced to a minimum. However, for saturator or condenser temperature control, since the temperature only varies slowly, it is generally unnecessary to use the full PID control scheme. A proportional-integral controller would more than suffice in most cases, and in some instances, a simple proportional control would be adequate. The means for temperature control is well known to those skilled in the art of electronic design, and any control circuit may be used in practice to achieve the desired result of keeping the saturator block 92 and condenser block 100 at their respective set-point values without departing substantially from the goals set forth in this invention to achieve consistent and repeatable performance of the CNC through improved design, and more precise temperature control of the saturator block and the condenser block as described above.

When using the CNC to count particles in an aerosol, sometimes there is the need to count several aerosols simultaneously. In such cases, it would be advantageous to use a single multi-channel CNC for such an application, rather than several individual CNCs.

The form of the counter in FIGS. 8 and 9 also can be made as a multi-channel counter. One advantage of a multi-channel CNC is that a single multi-channel device is generally much smaller than several separate stand-alone CNCs needed to perform the same measurement. The cost of the multi-channel device is also lower because a single electrical heating and control circuit can be used to control all the saturators, rather than separate heaters and controls, one for each of the stand-alone CNC. For the same reason, a single thermoelectric cooler and control circuit can be used to control all the condenser blocks, rather than separate cooling and control devices, one for each of the condenser blocks of separate CNCs.

Technically, a multi-channel CNC can also perform better because all the saturator chambers are in the same saturator block making the temperature and degree of vapor saturation in the sample gas streams to be more nearly the same. Similarly, the conditions for vapor condensation and droplet growth for all the sample streams would all be nearly the same, since the condenser chambers are formed in the same condenser block. The measurement made with a single multi-channel device would thus more consistent than measurement made with separate stand-alone CNCs.

Although the present invention has been described with reference to preferred embodiments, workers skilled in the art will recognize that changes may be made in form and detail without departing from the spirit and scope of the invention.

What is claimed is:

1. A continuous flow apparatus for detecting particles contained in a gas stream moving along a path, including:

a source of a working fluid in liquid form;

saturating means positioned along the path, for providing a vapor form of the working fluid to the gas stream, said saturating means including a porous metal in fluid communication with the fluid source and over which the gas stream passes;

a heated metal block in thermal contact with the porous metal and spaced from the working fluid to heat said porous metal, the porous metal extending from the heated metal block to contact the working fluid;

cooling means along the path of the gas stream and downstream of the saturating means to cause vapor condensation on the particles to form droplets in the gas stream; and a sensor downstream of the cooling means for detecting the droplets.

2. The apparatus of claim 1 wherein the porous metal has pores smaller than 500 μm in diameter.

3. A continuous flow apparatus for detecting particles in a gas stream, including:

a source of a gas sample moving in a stream along a path, said gas sample containing fine particles and water vapor;

a fluid source of a working fluid in liquid form;

a saturator comprising a passageway along the path and in fluid communication with the fluid source, and operable to provide working fluid vapor to the gas, a cooler along the path and downstream of the saturator to cause vapor to condense on the particles in the gas stream to form droplets;

a collector below the cooler to receive working fluid and water vapor condensing on the surface of the cooler and draining by gravity to the collector; and a sensor downstream of the cooler for detecting the droplets.

4. A continuous flow apparatus for detecting particles in a gas stream moving under pressure differentials, including:

a fluid source of a vaporizable working fluid in liquid form;

a saturator in fluid communication with the fluid source for providing working fluid vapor to the gas, said saturator including a porous material having a wall defining an interior space, and an orifice through which the gas stream moves to form a gas jet impinging into the interior space, said orifice having an area smaller than the cross-sectional area of the interior space;

a gas cooler receiving the gas stream downstream of the saturator to cool the gas to cause vapor condensation on the particles in the gas stream to form droplets; and a sensor downstream of the gas cooler carrying the gas and detecting the droplets.

5. The apparatus of claim 4 wherein the average gas velocity flowing through the orifice is at least 50 cm/sec.

6. The apparatus of claim 4 wherein at least two orifices are used in the inlet to the saturator.

7. A continuous flow apparatus for detecting particles in a gas stream, including:

a flow generator to draw a gas sample in a stream along a path through the apparatus;

a fluid source of a working fluid in liquid form in a container and the liquid having an upper level;

a saturator along the path and including a support block spaced from the upper level of the liquid with a fluid transfer element extending from the block to contact the liquid in the container to be in fluid communication with the fluid source for providing working fluid vapor to mix in the gas stream;

a condenser along the path and downstream of the saturator for causing vapor of the working fluid in the gas stream to condense on the particles to form droplets, said condenser including a chamber with cold walls and an inlet orifice for admitting the gas stream into the chamber, said orifice providing a gas jet impinging into the interior space of the chamber; and a sensor downstream of the condenser for detecting the droplets in the gas stream.

8. The apparatus of claim 7 wherein the average gas velocity flowing through the orifice is at least 50 cm/sec.

9. The apparatus of claim 8 wherein at least two orifices are used to form the inlet orifices.

10. The apparatus of claim 7 further including a thermoelectric module in thermal relation to a heat conducting support spaced from the liquid working fluid to selectively provide heating or cooling needed to keep the saturator at a desired temperature.

11. A continuous flow apparatus for detecting particles in a gas stream, including:

means to draw a gas sample in a gas stream along a path, said gas sample containing fine particles;

a source of a working fluid in liquid form in a supply container;

a saturator for providing working fluid vapor to the gas stream, said saturator including a thermoelectric module in thermal relation to a heat conducting support spaced from the liquid working fluid, the saturator having a first portion extending from the support to engage the liquid working fluid to conduct the working fluid to a second portion of the saturator;

a cooler along the path and downstream of the saturation means to cause vapor condensation on the particles to form droplets; and sensing means receiving the gas stream downstream of the cooler for detecting the droplets.

12. A continuous flow apparatus for detecting particles in a gas stream, including:

a flow inducing apparatus to draw a gas sample in a stream along first, second and third passageways connected in series, said gas sample containing fine particles;

a fluid source of a working fluid in liquid form;

a heater to heat the gas sample to a selected temperature while the gas stream moves along the first passageway;

a saturator having the second passageway connected to receive the gas stream from the first passageway, the saturator having a heated element in fluid communication with the working fluid for providing working fluid vapor to the gas stream as the gas stream moves through the second passageway; and a cooler having the third passageway to receive the gas stream from the second passageway to cause vapor condensation on particles in the gas stream to form droplets.

13. The continuous flow apparatus of claim 12, wherein an orifice is positioned between the first and second passageways to form a gas jet in the second passageway.

14. The continuous flow apparatus of claim 13, wherein a saturator heated element comprises a tube forming the second passageway, the tube being porous and having a portion in the working fluid source and other portions of the tube being spaced from the fluid source, the pores in the saturator causing capillary movement of the working fluid liquid to the surface of the second passageway.

15. The continuous flow apparatus of claim 14, wherein said tube is a porous metal tube, having a generally upright axis, the orifice between the first and second passageway being at an upper end of the tube, and the second passageway being connected to the third passageway with a tubular connector at a lower end of the third passageway.

16. The continuous flow apparatus of claim 14 and a plug in an interior of the tube spaced from the portion of the tube in the working fluid source to block the interior.

17. The continuous flow apparatus of claim 12, further characterized by an orifice between the second passageway and the third passageway, said third passageway carrying a gas jet formed by said orifice.

18. The continuous flow apparatus of claim 12, wherein the cooler comprises a block, and a thermoelectric cooler in heat conducting relation to the block.

19. The continuous flow apparatus of claim 12, and a sensor comprising a light scattering droplet counter connected to receive the gas stream from the third passageway.

20. A multi-channel, continuous flow apparatus for detecting particles in at least two separate gas streams, comprising a common fluid source containing a working fluid in liquid form for all channels, a common heating block for heating saturators for all channels, and a common cooling block to provide cooling for all channels, each channel of the apparatus being for detecting particles in a respective separate gas stream, each channel including:
- an apparatus creating a pressure differential to draw a gas sample in a stream along a path, said sample gas containing fine particles;
- a saturator in thermal contact with the common heating block along the path and in fluid communication with the common fluid source for providing working fluid vapor intermixed with the sample gas;
- a cooler in the form of a passageway in the common cooling block along the path and downstream of the saturator to cause vapor condensation on the particles to form droplets; and
- a particle detector downstream of the cooler for detecting droplets in the gas stream.

21. The apparatus of claim 20, wherein said saturator for each channel is supported on a support in close thermal contact with the saturator for each of the other channels and the saturators being held at substantially the same temperature.

22. The apparatus of claim 21, wherein said cooler for each channel is supported on the support in close thermal contact with the cooler of other adjacent channels and at substantially the same temperature.

* * * * *